United States Patent [19]
Lax et al.

[11] Patent Number: 5,569,242
[45] Date of Patent: Oct. 29, 1996

[54] METHOD AND APPARATUS FOR CONTROLLED CONTRACTION OF SOFT TISSUE

[76] Inventors: Ronald G. Lax, P.O. Box 2796, Grass Valley, Calif. 95945; Gary S. Fanton, 265 Golden Oak Dr., Portola Valley, Calif. 94028; Stuart D. Edwards, 1681 Austin Ave., Los Altos, Calif. 94024

[21] Appl. No.: 389,924

[22] Filed: Feb. 16, 1995

Related U.S. Application Data

[63] Continuation of Ser. No. 238,862, May 6, 1994, Pat. No. 5,458,596.

[51] Int. Cl.$^6$ ........................... A61B 17/36
[52] U.S. Cl. ........................... 606/42; 606/31; 606/34; 606/41; 606/49; 607/99; 607/102; 607/149; 607/153; 128/898
[58] Field of Search .............. 128/898; 606/27, 606/31, 32–34, 40–42, 49, 50; 607/96, 98–102, 115, 116, 148, 149, 153, 154

[56] References Cited

U.S. PATENT DOCUMENTS

| | | |
|---|---|---|
| 4,326,529 | 4/1982 | Doss et al. . |
| 4,375,220 | 3/1983 | Matvias . |
| 4,381,007 | 4/1983 | Doss . |
| 4,397,314 | 8/1983 | Vaguine . |
| 4,517,975 | 5/1985 | Garito et al. . |
| 4,593,691 | 6/1986 | Lindstrom et al. . |
| 4,907,589 | 3/1990 | Cosman . |
| 4,976,709 | 12/1990 | Sand . |
| 5,103,804 | 4/1992 | Abele et al. . |
| 5,191,883 | 3/1993 | Lennox et al. . |
| 5,213,097 | 5/1993 | Zeindler . |
| 5,230,334 | 7/1993 | Klopotek . |
| 5,261,906 | 11/1993 | Pennino et al. . |
| 5,323,778 | 6/1994 | Kandarpa et al. . |
| 5,334,193 | 8/1994 | Nardella . |
| 5,348,554 | 9/1994 | Imran et al. . |
| 5,458,596 | 10/1995 | Lax et al. ................ 606/41 |

FOREIGN PATENT DOCUMENTS

| | | |
|---|---|---|
| 0479482 | 4/1992 | European Pat. Off. . |
| WO93/01774 | 7/1992 | WIPO . |

*Primary Examiner*—David M. Shay
*Attorney, Agent, or Firm*—Wilson Sonsini Goodrich & Rosati

[57] ABSTRACT

An apparatus and method are provided for control contraction of tissue that includes collagen fibers. The apparatus includes a handpiece, and an electrode with an electrode proximal end associated with the handpiece. A distal end of the electrode has a geometry that delivers a controlled amount of energy to the tissue for a desired contraction of the collagen fibers. This is achieved while dissociation and breakdown of the collagen fibers is minimized. The handpiece, with electrode, is adapted to be introduced through an operating cannula in percutaneous applications. Additionally, an operating cannula may be included in the apparatus and be attached to the handpiece. The apparatus and method provides for a desired level of contraction of collagen soft tissue without dissociation or breakdown of collagen fibers.

15 Claims, 15 Drawing Sheets

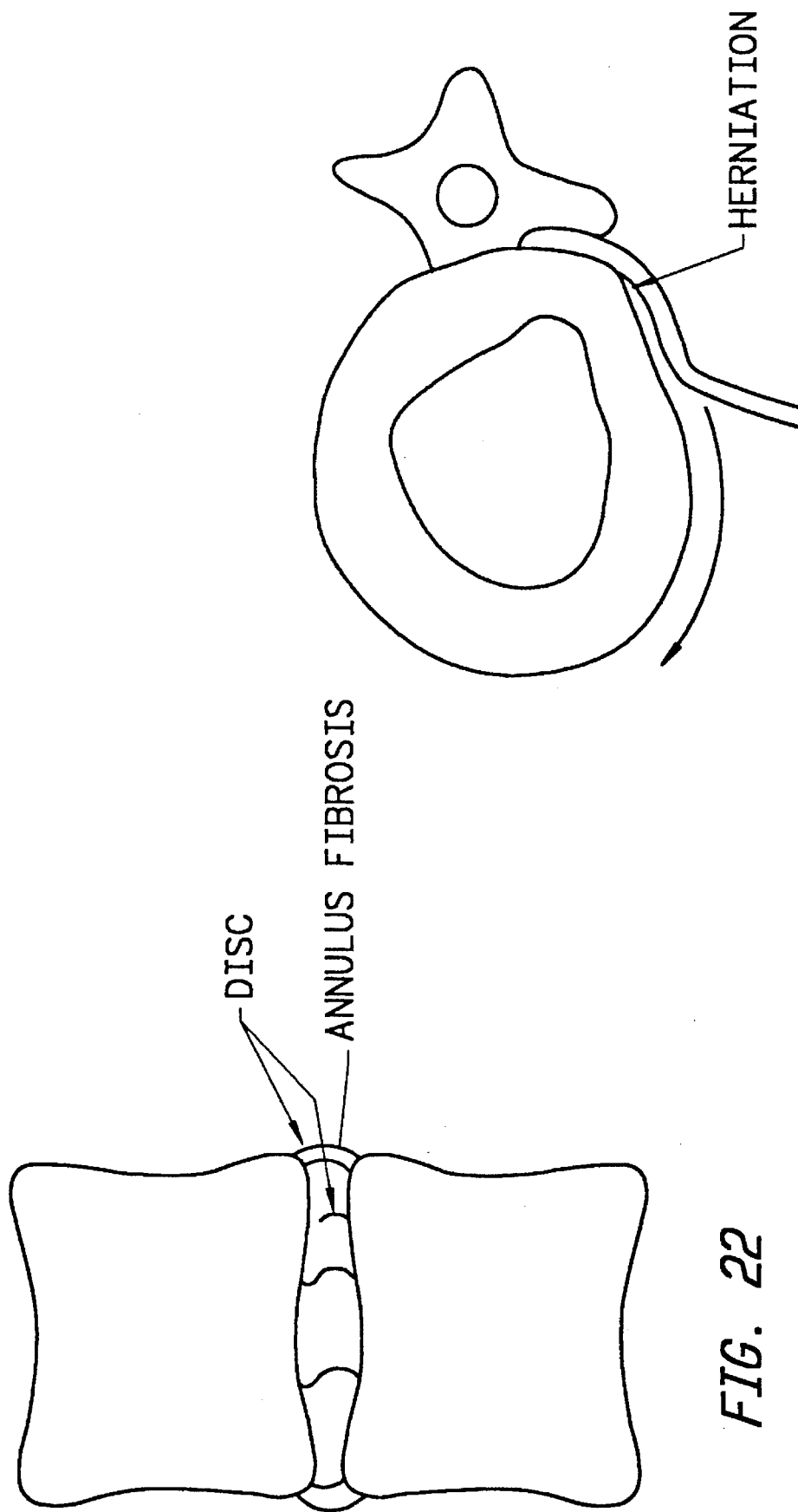

METHOD AND APPARATUS FOR CONTROLLED CONTRACTION OF SOFT TISSUE

This application is a continuation, of Application Ser. No. 08/238,862, filed May 6, 94, U.S. Pat. No. 5,458,596.

BACKGROUND OF THE INVENTION

1. Field of the Invention

This invention relates generally to the contraction of soft tissue, and more particularly, to the compaction of soft collagen tissue with minimal dissociation of collagen tissue.

2. Description of the Related Art

Instability of peripheral joints has long been recognized as a significant cause of disability and functional limitation in patients who are active in their daily activities, work or sports. Diarthrodial joints of musculoskeletal system have varying degrees of intrinsic stability based on joint geometry and ligament and soft tissue investment. Diarthrodial joints are comprised of the articulation of the ends of bones and their covering of hyaline cartilage surrounded by a soft tissue joint capsule that maintains the constant contact of the cartilage surfaces. This joint capsule also maintains within the joint the synovial fluid that provides nutrition and lubrication of the joint surfaces. Ligaments are soft tissue condensations in or around the joint capsule that reinforce and hold the joint together while also controlling and restricting various movements of the joints. The ligaments, joint capsule, and connective tissue are largely comprised of collagen.

When a joint becomes unstable, its soft tissue or bony structures allow for excessive motion of the joint surfaces relative to each other and in directions not normally permitted by the ligaments or capsule. When one surface of a joint slides out of position relative to the other surface, but some contact remains, subluxation occurs. When one surface of the joint completely disengages and loses contact with the opposing surface, a dislocation occurs. Typically, the more motion a joint normally demonstrates, the more inherently loose the soft tissue investment is surrounding the joint. This makes some joints more prone to instability than others. The shoulder, (glenohumeral) joint, for example, has the greatest range of motion of all peripheral joints. It has long been recognized as having the highest subluxation and dislocation rate because of its inherent laxity relative to more constrained "ball and socket" joints such as the hip.

Instability of the shoulder can occur congenitally, developmentally, or traumatically and often becomes recurrent, necessitating surgical repair. In fact subluxations and dislocations are a common occurrence and cause for a large number of orthopedic procedures each year. Symptoms include pain, instability, weakness, and limitation of function. If the instability is severe and recurrent, functional incapacity and arthritis may result. Surgical attempts are directed toward tightening the soft tissue restraints that have become pathologically loose. These procedures are typically performed through open surgical approaches that often require hospitalization and prolonged rehabilitation programs.

More recently, endoscopic (arthroscopic) techniques for achieving these same goals have been explored with variable success. Endoscopic techniques have the advantage of being performed through smaller incisions and therefore are usually less painful, performed on an outpatient basis, are associated with less blood loss and lower risk of infection and have a more cosmetically acceptable scar. Recovery is often faster postoperatively than using open techniques. However, it is often more technically demanding to advance and tighten capsule or ligamentous tissue arthroscopically because of the difficult access to pathologically loose tissue and because it is very hard to determine how much tightening or advancement of the lax tissue is clinically necessary. In addition, fixation of advanced or tightened soft tissue is more difficult arthroscopically than through open surgical methods.

Collagen connective tissue is ubiquitous in the human body and demonstrates several unique characteristics not found in other tissues. It provides the cohesiveness of the musculoskeletal system, the structural integrity of the viscera as well as the elasticity of integument. These are basically five types of collagen molecules with Type I being most common in bone, tendon, skin and other connective tissues, and Type III is common in muscular and elastic tissues.

Intermolecular cross links provide collagen connective tissue with unique physical properties of high tensile strength and substantial elasticity. A previously recognized property of collagen is hydrothermal shrinkage of collagen fibers when elevated in temperature. This unique molecular response to temperature elevation is the result of rupture of the collagen stabilizing cross links and immediate contraction of the collagen fibers to about one-third of their original lineal distention. Additionally, the caliber of the individual fibers increases greatly, over four fold, without changing the structural integrity of the connection tissue.

There has been discussion in the existing literature regarding alteration of collagen connective tissue in different parts of the body. One known technique for effective use of this knowledge of the properties of collagen is through the use of infrared laser energy to effect tissue heating. The use of infrared laser energy as a corneal collagen shrinking tool of the eye has been described and relates to laser keratoplasty, as set forth in U.S. Pat. No. 4,976,709. The importance controlling the localization, timing and intensity of laser energy delivery is recognized as paramount in providing the desired soft tissue shrinkage effects without creating excessive damage to the surrounding non-target tissues.

Radiofrequency (RF) electrical current has been used to reshape the cornea. Such shaping has been reported by Doss in U.S. Pat. Nos. 4,326,529; and 4.381,007. However, Doss was not concerned with dissociating collagen tissue in his reshaping of the cornea.

Shrinkage of collagen tissue is important in many applications. One such application is the shoulder capsule. The capsule of the shoulder consists of a synovial lining and three well defined layers of collagen. The fibers of the inner and outer layers extend in a coronal access from the glenoid to the humerus. The middle layer of the collagen extends in a sagittal direction, crossing the fibers of the other two layers. The relative thickness and degree of intermingling of collagen fibers of the three layers vary with different portions of the capsule. The ligamentous components of the capsule are represented by abrupt thickenings of the inner layer with a significant increase in well organized coarse collagen bundles in the coronal plane.

The capsule functions as a hammock-like sling to support the humeral head. In pathologic states of recurrent traumatic or developmental instability this capsule or pouch becomes attenuated and the capsule capacity increases secondary to capsule redundance. In cases of congenital or developmental multi-directional laxity, an altered ratio of type I to type III collagen fibers may be noted. In these shoulder capsules a higher ratio of more elastic type III collagen has been described.

There is a need for a method and apparatus to effect controlled lineal contraction or shrinkage of collagen fibers to provide a multitude of non-destructive and beneficial structural changes and corrections within the body. More particularly with regard to the shoulder capsule, current surgical techniques involve cutting or advancing the shoulder capsule to eliminate capsular redundance or to otherwise tighten the ligamous complex. Accordingly, there is a need to control shrinkage of the capsule by utilizing the knowledge of the properties of collagen in response to a specific level of thermal application.

SUMMARY OF THE INVENTION

It is an object of the present invention to provide a method and apparatus to control the duration and application of thermal energy to a tissue site made that includes collagen soft tissue; a desired level of contraction of collagen fibers is obtained while dissociation and breakdown of the collagen fibers is minimized.

Another object of the present invention is to use RF heating in a fluid environment to control thermal spread to a tissue that includes collagen soft tissue, and a desired contraction of collagen fibers is obtained while minimizing dissociation and breakdown of the collagen fibers.

Yet another object of the present invention is to provide a device directed to collagen connective tissue shrinkage by the use of RF heating to a temperature profile of 43 to 90 degrees centigrade.

Another object of the present invention is to provide a device directed to collagen connective tissue shrinkage by the use of RF heating to a temperature profile of 43 to 75 degrees centigrade.

Still a further object of the present invention is to provide a device directed to collagen connective tissue shrinkage by the use of the RF heating to a temperature profile of 45 to 60 degrees centigrade.

Another object of the present invention is to provide an apparatus which delivers RF energy through an endoscopically guided handpiece in a fluid environment to obtain maximum contraction of collagen soft tissue while minimizing dissociation and breakdown of the collagen tissue.

Yet another object of the present invention is to provide an apparatus that provides for the maximum amount of collagen contraction without dissociation of the collagen structure.

Another object of the present invention is to provide an apparatus to deliver a controlled amount of RF energy to the collagen soft tissue of a joint in order to contract and restrict the soft tissue elasticity and improve joint stability.

A further object of the present invention to provide an apparatus and method that reduces redundancy of the shoulder capsule and improves stability to the joint.

These and other objects of the invention are obtained with an apparatus for control contraction of tissue that includes collagen fibers. The apparatus include a handpiece, and an electrode with an electrode proximal end that is associated with the handpiece. A distal end of the electrode has a geometry that delivers a controlled amount of energy to the tissue in order to achieve a desired contraction of the collagen fibers. This is achieved while dissociation and breakdown of the collagen fibers is minimized.

The handpiece, with electrode, is adapted to be introduced through an operating cannula in percutaneous applications. Additionally, it may be desirable to include as part of the apparatus an operating cannula. In this instance, the operating cannula has a proximal end that attaches to the handpiece, and a distal end that is adapted to be introduced into a body structure. The electrode is positioned within the operating cannula, and extendable beyond the distal end of the cannula when thermal energy is delivered to the tissue.

It is recognized that the delivery of the thermal energy to the tissue should be delivered in such a way that none of the tissue is ablated. Additionally, the delivery is achieved without dissociating or breaking down the collagen structure. This can be accomplished in different ways, but it has been discovered that an electrode with radiused edges at its distal end is suitable to obtain this result. The present invention is applicable to a number of different anatomical sites. Depending on the anatomy, it may be necessary to deflect the distal end of the electrode to reach the desired site. Additionally, one side of the electrode may include an insulating layer so that thermal energy is only delivered to the intended tissue, and not a tissue in an adjacent relationship to the area of treatment.

In certain instances it is desirable to be able to vary the length of the electrode conductive surface which delivers the thermal energy to the tissue. For this purpose, an adjustable insulator, that is capable of movement along the longitudinal axis of the electrode, provides a way of adjusting the length of electrode conductive surface.

Memory metals can be used for the electrode construction. An advantage of memory metals is that with the application of heat to the metal, it can be caused to be deflected. This is particularly useful for deflecting the distal end of the electrode.

The electrode can include a central lumen that receives an electrolytic solution from an electrolytic source. A plurality of apertures are formed in the distal end of the electrode and deliver the flowing electrolytic fluid to the tissue. Instead of an electrolytic solution, an electrolytic gel can also be introduced through the electrode.

In one embodiment of the invention, the electrode is partially surrounded by an insulating housing in order to position the electrode in an adjacent but spaced relationship to the tissue. A portion of the insulating housing rides on the tissue, and creates the equivalent of a partial dam for electrolytic solution introduced through the electrode and towards the tissue. A cuff is disposed about the insulating housing. The cuff and insulating housing together create a return electrolytic solution channel for the removal of solution flowing out of the dam and away from the tissue site.

The handpiece of the invention can be connected, with a cable, to an RF energy source. A closed loop feedback system can be included and coupled to a temperature sensor on the electrode and the RF energy source. Temperature at the electrode can be monitored, and the power of the RF energy source adjusted to control the amount of energy that is delivered to the tissue.

The present invention has wide spread application to many different anatomical locations. It can be utilized for controlled contraction of collagen soft tissue of a joint capsule, particularly the gleno-humoral joint capsule of the shoulder, to treat herniated discs, the meniscus of the knee, for dermatology, to name just a few.

In one embodiment of the invention, RF heating in a fluid or saline environment is used to control thermal spread to soft collagen tissue. The RF energy can be delivered through an endoscopically guided handpiece under arthroscopic visualization by the surgeon. In the temperature range of 43 to 90 degrees C., maximum collagen contraction is achieved. Additional temperature ranges are 43 to 75 degrees C., and 45 to 60 degrees C. Lower temperatures do not provide maximum thermal induced contracture of the collagen fibrils. Greater temperatures create excessive destruction and disintegration of the collagen fibrillar pattern. Thus, the present invention is a method and apparatus which accurately controls the application of heat within a desired thermal range. This heat is delivered the collagen soft tissue, thereby contracting and restricting the soft tissue elasticity and improving stability.

DESCRIPTION OF THE DRAWINGS

FIG. 22 is a sectional view of a disc positioned between two vertebrae.

FIG. 23 is a schematic drawing of the apparatus of the invention with an electrode supplying thermal energy to a herniated disc.

DETAILED DESCRIPTION OF THE PREFERRED EMBODIMENTS

Figure 1:
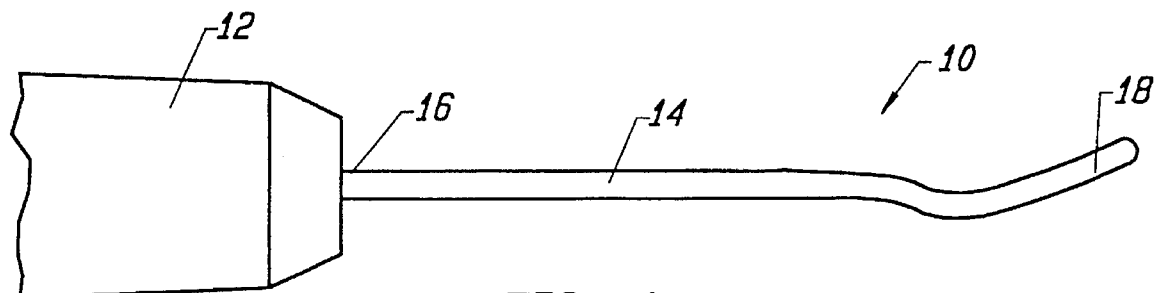
FIG. 1 is a perspective plan view of an apparatus for control contraction of tissue that includes collagen fibers, including a handpiece and an electrode, according to the invention.

Referring now generally to FIG. 1, an apparatus for control contraction of tissue that includes collagen fibers is generally denoted as 10. Apparatus 10 includes a handpiece 12 that is preferably made of an insulating material. Types of such insulating materials are well known in those skilled in the art; An electrode 14 is associated with handle 12 at a proximal end 16 of electrode 14, and may even be attached thereto. A distal end 18 of electrode 14 has a geometry that delivers a controlled amount of energy to the tissue in order to achieve a desired level of contraction of the collagen fibers. Contraction is achieved while dissociation and breakdown of the collagen fibers is minimized.

Figure 2:
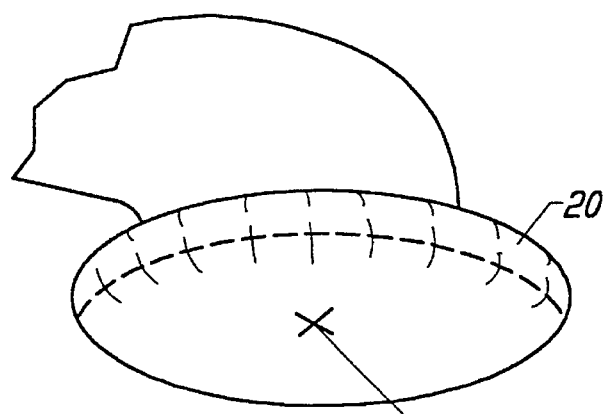
FIG. 2 is a perspective plan view of a distal end of the electrode with all edges radiused according to the invention.
Figure 3:
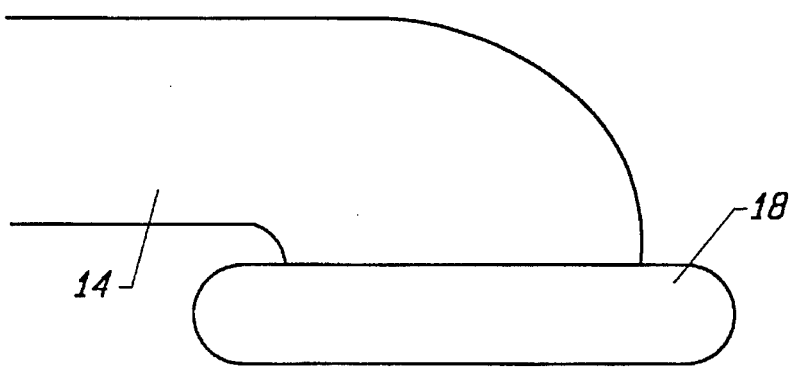
FIG. 3 is a side view of the distal end of the electrode of FIG. 2.
Figure 4:
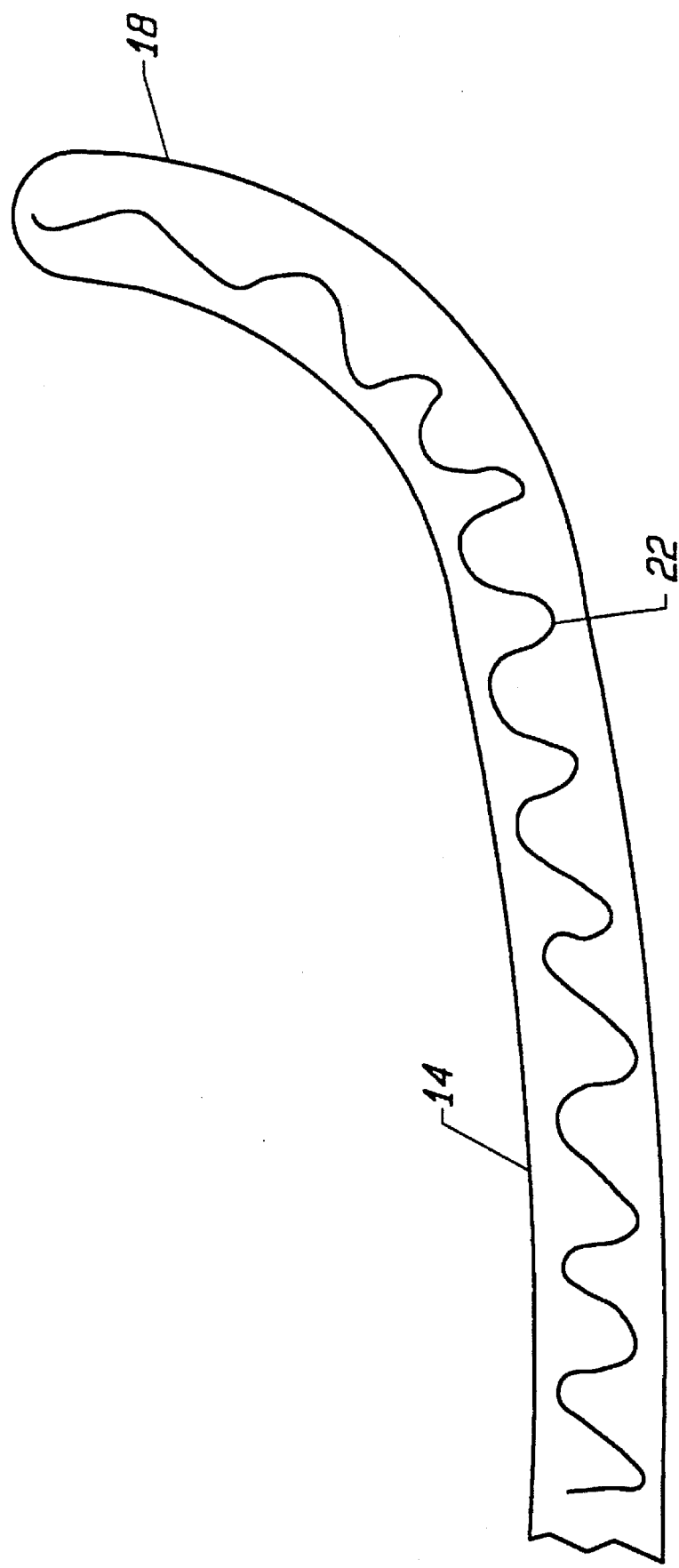
FIG. 4 is a sectional view of the deflected electrode with a resistive heating element positioned in an interior lumen of the electrode according to the invention.

Electrode 14 can have be a flat elongated structure that is easily painted across a tissue without "hanging up" on any section of the tissue. In one geometry of electrode 14, all edges 20 of distal end 18 are radiused, as illustrated in FIGS. 2 and 3. Distal end 18 can have a variety of geometric configurations. One such geometry is a disc shaped geometry without square edges. Electrode 14 can be made of a number of different materials including but not limited to stainless steel, platinum, other noble metals and the like. Electrode 14 can be made of a memory metal, such as nickel titanium, commercially available from Raychem Corporation, Menlo Park, Calif. In FIG. 4, a resistive heating element 22 can be positioned in an interior lumen of electrode 14. Resistive heating element can be made of a suitable metal that transfers heat to electrode 14, causing electrode distal end 18 to become deflected when the temperature of electrode 14 reaches a level that the memory metal is caused to deflect, as is well known in the art. Not all of electrode 14 need be made of the memory metal. It is possible that only electrode distal end 18 be made of the memory metal in order to effect the desired deflection. There are other methods of deflecting electrode 18, as will be more fully discussed and described in a later section of this specification.

Apparatus 10, comprising handpiece 12 and electrode 14, is adapted to be introduced through an operating cannula for percutaneous applications. It will be appreciated that apparatus 10 may be used in non-percutaneous applications and that an operating cannula is not necessary in the broad application of the invention.

Figure 5:
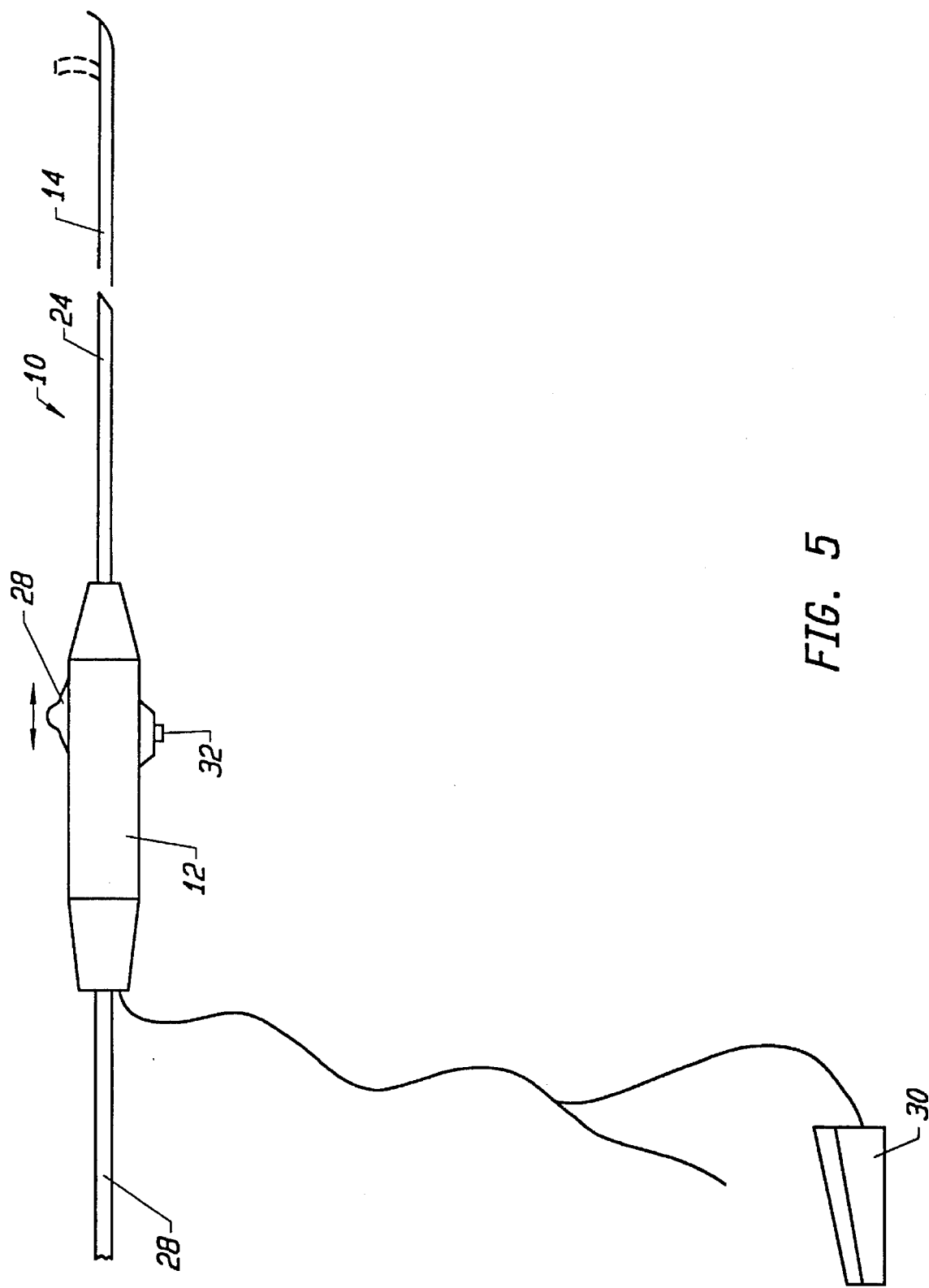
FIG. 5 is a perspective plan view of the apparatus for control contraction of tissue with collagen fibers with a handpiece, electrode and an operating cannula according to the present invention.
Figure 6:
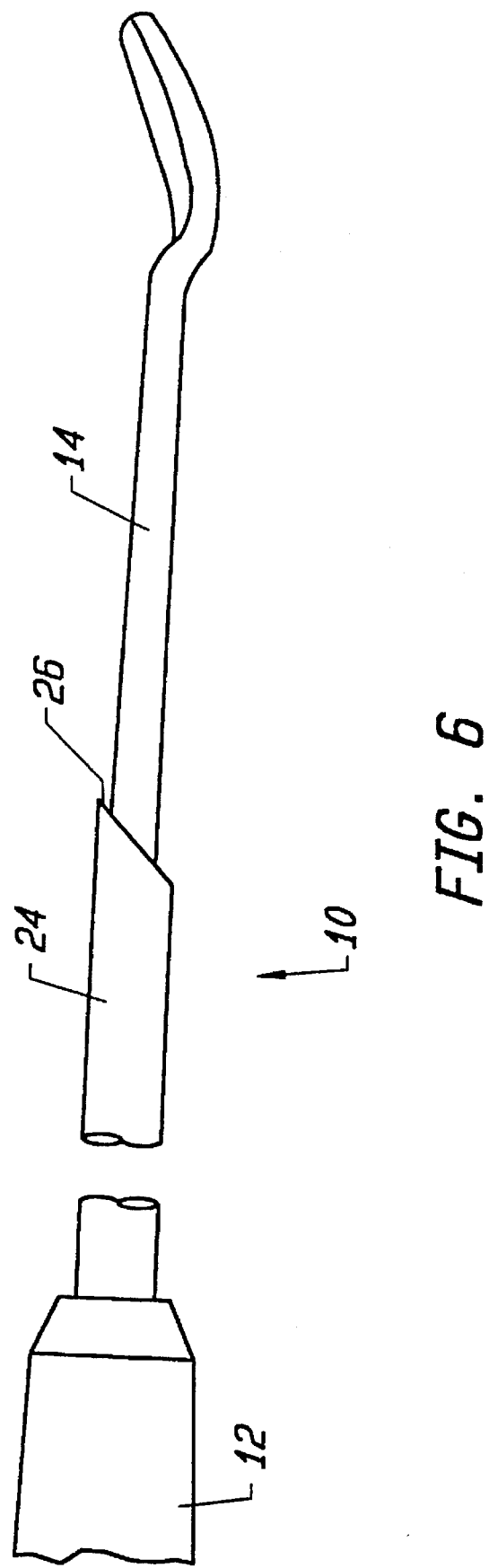
FIG. 6 is a close up perspective plan view of the distal end of the electrode of the apparatus of FIG. 5 according to the invention.

As illustrated in FIGS. 5 and 6, apparatus 10 can also include, as an integral member, an operating cannula 24 which can be in the form of a hyperdermic trocar with dimensions of about 3 to 6 mm outside diameter, with tubular geometries such as those of standard commercially available operating cannulas. Operating cannula 24 can be made of a variety of biocompatible materials including but not limited to stainless steel, and the like.

Operating cannula 24 has a proximal end that attaches to handpiece 12 and it can have a sharp or piercing distal end 26 that pierces a body structure in order to introduce electrode 14 to a desired site. Electrode 14 is positioned within an interior lumen of operating cannula 24 and is extendable beyond distal end 26 in order to reach the desired tissue site. Electrode 14 can be advanced and retracted in and out of operating cannula 24 by activating a deployment button 28 which is located on the exterior of handle 12. Deployment button 28 is preferably activated by the operator merely by sliding it, which causes electrode 14 to advance in a direction away from distal end 26 of operating cannula 24. Deployment button 28 can be pulled back, causing a retraction of electrode 14 towards distal end 26. In many instances, electrode 14 will be retracted to be positioned entirely within operating cannula 14. Electrode 14 can also deployed with fluid hydraulics, pneumatics, servo motors, linear actuators, and the like.

An electrical and/or fluid flow cable 28 attaches to handle 12 and provides the necessary connection of apparatus 10 to a suitable energy source and/or a source of fluid, which may be an electrolytic solution or an electrolytic gel. An electrolytic solution, for purposes of this invention, is one that increases the transfer of thermal energy from electrode 14 to a tissue. Suitable electrolytic solutions include but are not limited to saline solution and the like.

A variety of energy sources can be used with the present invention to transfer thermal energy to the tissue that includes collagen fibers. Such energy sources include but are not limited to RF, microwave, ultrasonic, coherent light and thermal transfer.

When an RF energy source is used, the physician can activate the energy source by the use of a foot switch 30 that is associated with handle 12 and electrode 14. Significantly, a controlled amount of RF energy is delivered so that there is an effective transfer of thermal energy to the tissue site so that the thermal energy spreads widely through the tissue but does not cause a dissociation or breakdown of the collagen fibers.

For many applications, it is necessary to have electrode distal end 18 to become deflected (FIG. 6). This can be achieved with the use of memory metals, or it can be accomplished mechanically. A steering wire, or other mechanical structure, is attached to either the exterior or interior of electrode 14. A deflection button 32, located on handle 12, is activated by the physician, causing steering wire 34 (FIG. 7) to tighten, and impart an retraction of electrode 14, resulting in a deflection of electrode distal end 18. It will be appreciated that other mechanical mechanisms can be used in place of steering wire 34. The deflection may be desirable for tissue sites that have difficult access, and it is necessary to move about a non-linear tissue. By deflecting electrode distal end 18, the opportunity to provide more even thermal energy to a tissue site is achieved, and the possibility of ablating or dissociation of collagen material is greatly reduced.

Figure 7:
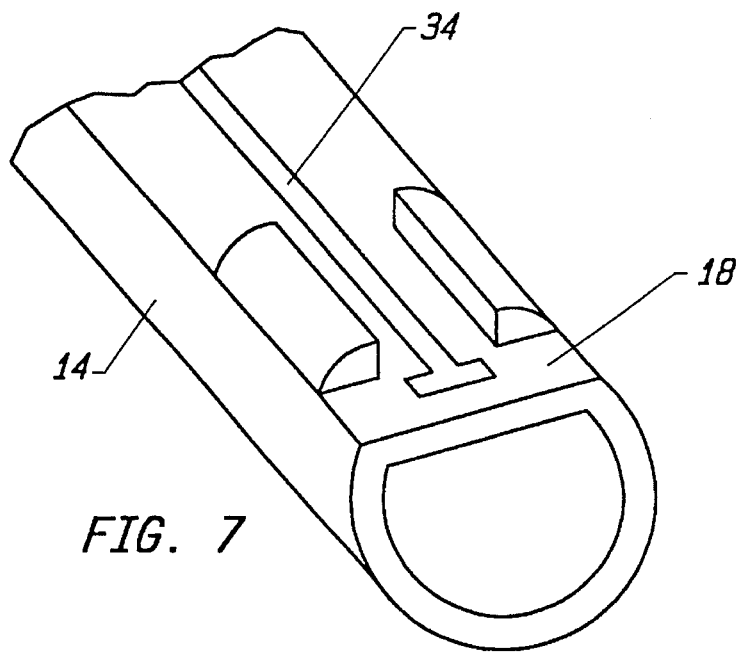
FIG. 7 is a perspective plan view of an electrode with a steering wire positioned on the exterior of the electrode according to the invention.
Figure 8:
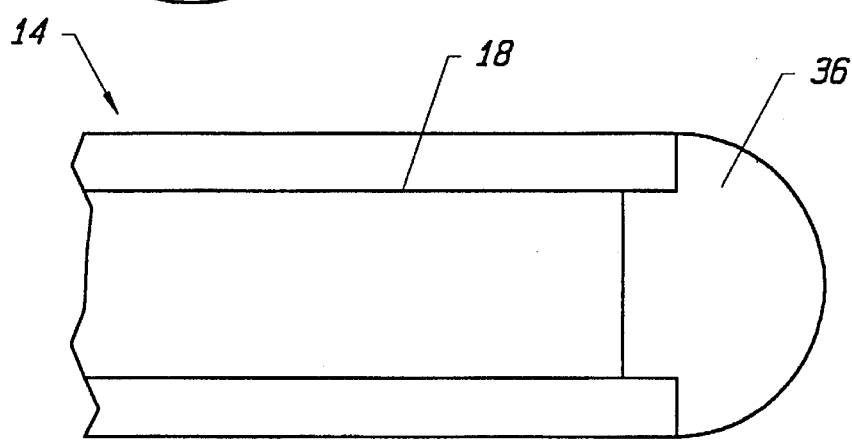
FIG. 8 is a sectional view of an electrode with a lumen and a plug that is attached to the electrode distal end according to the invention.

As shown in FIG. 7, steering wire 34 attaches to a flat formed on the exterior of electrode 14. Wire EDM technology can be used to form the flat on electrode 14. A "T" bar configuration is illustrated in FIG. 7. Chemical etching may be used to create the "T" bar. Steering wire 34 need not be an actual wire. It can also be a high tensile strength cord such as Kevlar. Steering wire 34 can be made of stainless steel flat wire, sheet material, and the like.

Electrode 14 can be tubular in nature with a central lumen. Electrode distal end 18 can include a conductive plug that is sealed to electrode distal end 18 by welding, e-beam, laser, and the like.

Figure 9:
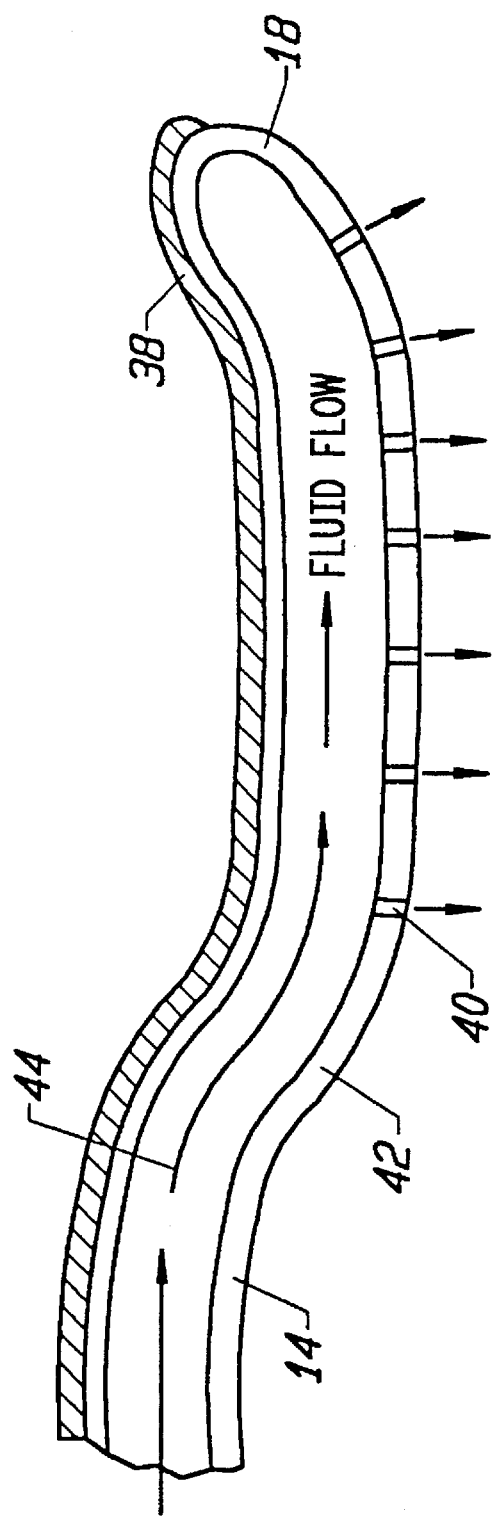
FIG. 9 is a cross sectional view of an electrode with fluid flowing through an interior lumen of the electrode according to the invention.

In FIG. 9, Electrode 14 can include an electrical insulation layer 38 formed on a back side of electrode 14 which is intended to minimize damage to tissue areas that are not treated. For example, when electrode 14 is introduced into a tight area, and only one surface of the tight area is to be treated, then it desirable to avoid delivering thermal energy to other tissue site areas. The inclusion of insulation layer 38 accomplishes this result. Suitable insulation materials include but are not limited to polyimide, epoxy varnish, PVC and the like. Electrode 14 includes a conductive surface 40 which does not include insulation layer 38.

A plurality of apertures 42 are formed in electrode 14 to introduce a flowing fluid 44 through an interior lumen of electrode 14 and to the tissue site. The flowing fluid can be an electrolytic solution or gel, including but not limited to saline. The electrolyte furnishes an efficient electrical path and contact between electrode 14 and the tissue to be heated.

Figure 10:
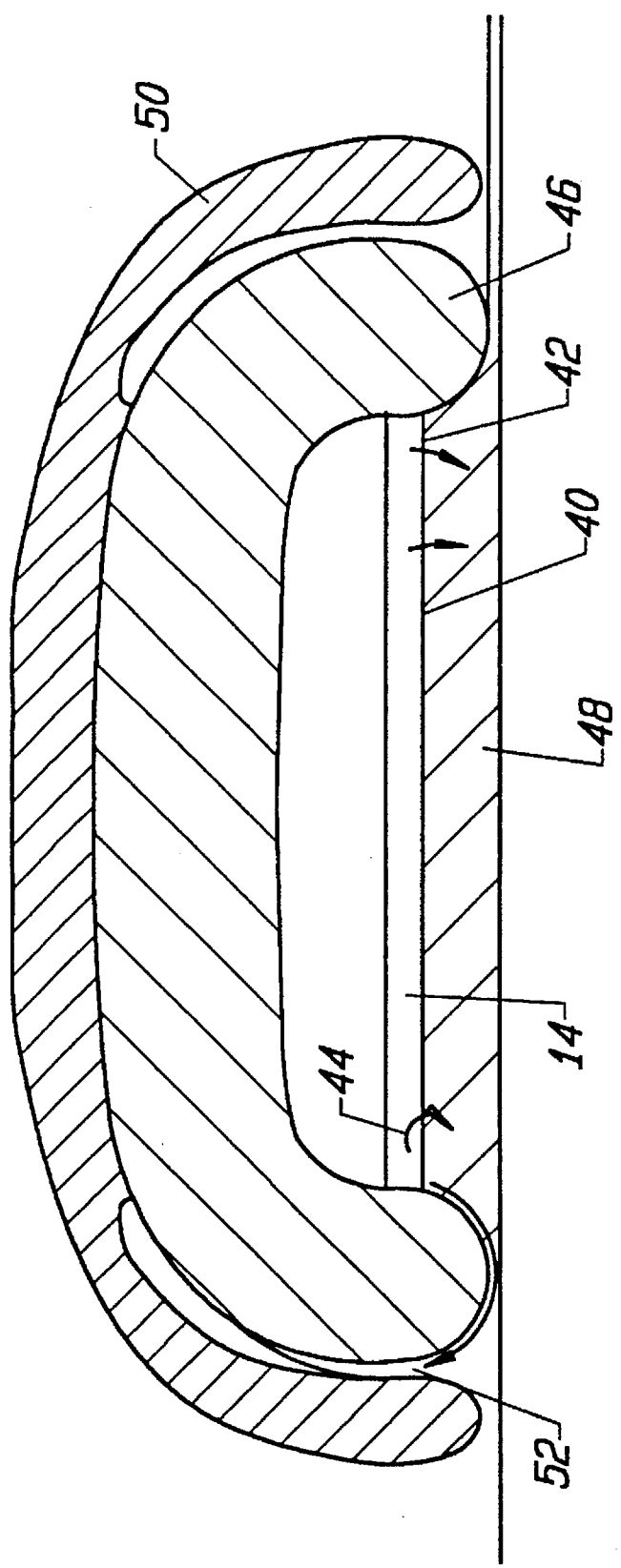
FIG. 10 is a cross sectional view of an RF electrode structure with an insulating housing surrounding a portion of an electrode, and a cuff surrounding the insulating housing according to the invention.

Referring now to FIG. 10, electrode 14 includes a central lumen for receiving an electrolytic solution 44 from an electrolytic source. Electrolytic solution 44 flows from electrode 14 through a plurality of apertures 42 formed in conductive surface 40. An insulating housing 46 surrounds electrode 14, leaving only conductive surface 40 exposed. Insulating housing 46 can be formed of a variety of non-electrically conducting materials including but not limited to thermoplastics, thermosetting plastic resins, ceramics, and the like. Insulating housing 46 rides along the surface of the tissue to be treated and positions conductive surface 40 in an adjacent but spaced relationship with the tissue. In this manner, there isn't direct contact of conductive surface 40 with the tissue, and the chance of dissociation or break down of the collagen fibers is reduced. Insulating housing 46 creates a partial dam 48 of electrolytic solution adjacent to the tissue. Electrical energy is transferred from electrode 14 to electrolytic solution 44, and from electrolytic solution 44 in dam 48 to the tissue. A cuff 50 surrounds insulating housing 46. Cuff 50 may be made of a variety of materials including but not limited to thermoplastic, thermosetting plastic resins, ceramics and the like. The respective dimensions of insulating housing 46 and cuff can vary according to the specific application. For example, in percutaneous applications, the dimensions will be smaller than for those used in topical applications such as dermatology.

Cuff 50 and insulating housing 46 are closely positioned to each other, but they are spaced in a manner to create a return electrolytic solution channel 52. The used electrolyte solution may either be released within a confined body area, such as the joint, or not be returned to the tissue, but instead is removed.

Use of a cooled solution to deliver the thermal energy to the tissue, instead of direct contact with conductive surface 40, provides a more even thermal gradient in the tissue. Avoidance of surface overheating can be accomplished. There is a more uniform level of thermal energy applied to the tissue. Electrolytic solution 44 may be cooled in the range of about 30 to 55 degrees C.

Figure 11:
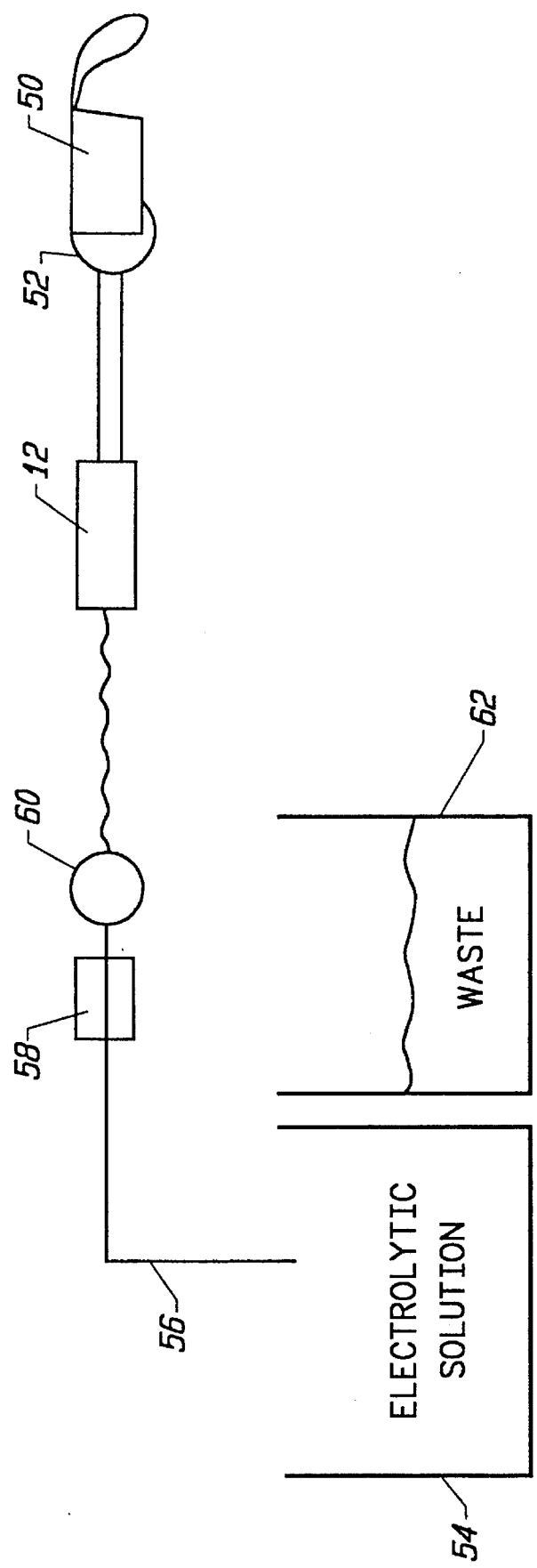
FIG. 11 is a block diagram of a fluid control system useful with the electrode structure of FIG. 10 according to the invention.

Referring now to FIG. 11, electrolytic solution 44 is in a holding container 54 and transferred through a fluid conduit 56 to a temperature controller 58 which can cool and heat electrolytic solution 44 to a desired temperature. A pump 60 is associated with fluid conduit 56 to transfer fluid throughout the system and delivers electrolytic solution 44 through handpiece 12 to electrode 14. Returning electrolytic fluid 44 passes through return electrolytic solution channel 52, and is delivered to a waste container 62. The flow rate of electrolytic solution can be in the range of less than about 1 cc/min. to greater than 5 cc/second.

Figure 12:
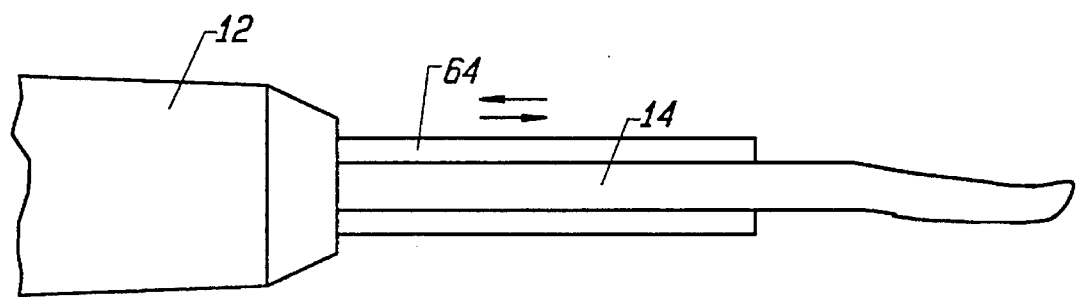
FIG. 12 is a perspective plan view of a handpiece, an electrode and a sleeve that slides across the surface of the electrode to vary the amount of electrode conductive surface according to the invention.

The area of electrode 14 that serves as conductive surface 44 can be adjusted by the inclusion of an insulating sleeve 64 (FIG. 12) that is positioned around electrode 14. Sleeve 64 is advanced and retracted along the surface of electrode 14 in order to provide increase or decrease the surface area of conductive surface 44 that is directed to the tissue. Sleeve 64 can be made of a variety of materials including but not limited to nylon, polyimides, other thermoplastics and the like. The amount of available conductive surface 44 available to deliver thermal energy can be achieved with devices other than sleeve 64, including but not limited to printed circuitry with multiple circuits that can be individually activated, and the like.

Figure 13:
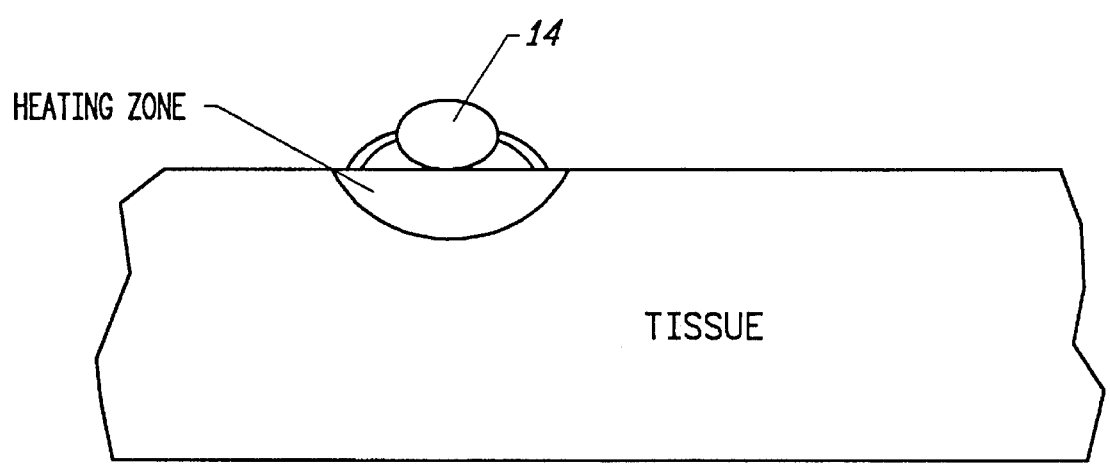
FIG. 13 is a sectional view of an electrode with an oval cross section and the heating zone in the tissue according to the invention.

Electrode 14 can have a variety of different geometric configurations. In one embodiment, electrode 14 has an oval cross section (FIG. 13). The oval cross section provides a greater conductive surface 44 area that is in contact with the tissue. A larger zone of heating to the tissue is provided. The thermal gradient within the tissue is more even and the possible dissociation or breakdown of the collagen fibers is reduced.

Figure 15:
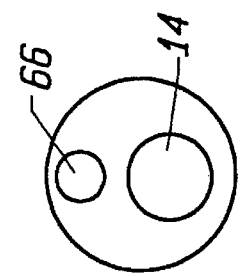
FIG. 15 is a cross sectional view of the device of FIG. 14, taken along the lines 15—15 according to the invention.
Figure 14:
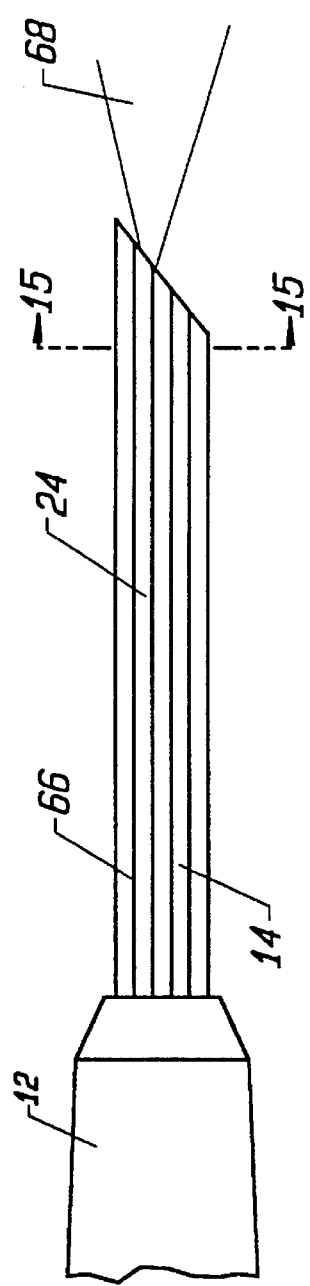
FIG. 14 is a sectional view of a handle, electrode, operating cannula and a viewing scope, with the viewing scope and electrode positioned in the operating cannula according to the invention.

As illustrated in FIG. 14, operating cannula 24 includes a viewing scope 66 which may be positioned above electrode 14 (FIG. 15). Viewing scope 66 provides a field of view 68, permitting the surgeon to view while delivering energy to the tissue site and contracting the tissue. Viewing scope 66 can include a bundle light transmitting fibers and optical viewing elements. Alternatively, the surgeon can view the procedure under arthroscopic visualization.

Figure 16:
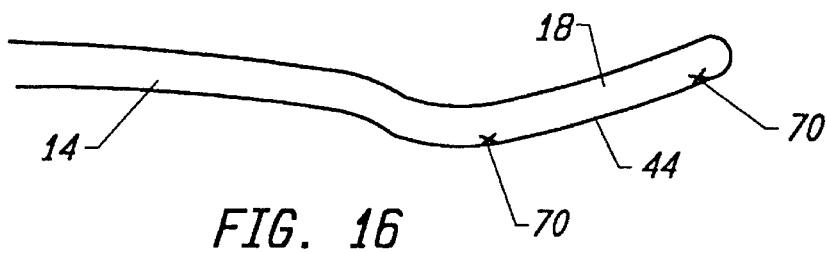
FIG. 16 is a perspective plan view of an electrode distal end with temperature sensors positioned in the distal end according to the invention.

Referring now to FIG. 16, one or more temperature sensors 70 can be positioned in electrode 14, particularly at electrode distal end 18. Temperature sensor 70 can be a thermocouple, a thermistor or phosphor coated optical fibers. Temperature sensor 70 can be utilized to determine the temperature of electrode 14, particularly at conductive surface 40, or temperature sensor 70 may be employed to determine the temperature of the tissue site.

Figure 17:
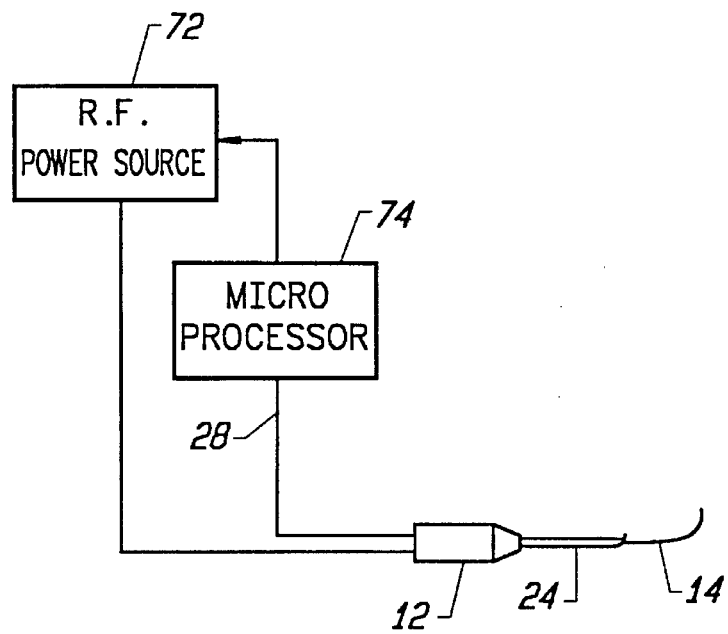
FIG. 17 is a block diagram of a closed loop feedback system according to the invention.

Additionally, the apparatus of the present invention can be an RF energy delivery device to effect contraction of collagen soft tissue while minimizing dissociation or breakdown of the collagen fibers. As shown in FIG. 17 the apparatus for control contraction of collagen soft tissue can include handpiece 12, electrode 14, operating cannula 24, a cable 28 and an RF power source 72. Suitable RF power sources are commercially available and well known to those skilled in the art. In one embodiment of the invention RF power source 72 has a single channel, delivering approximately 30 watts of RF energy and possess continued flow capability. A closed loop feedback system, coupling temperature sensor 70 to RF energy source 72 can be included. The temperature of the tissue, or of electrode 14 is monitored, and the power of RF generator 72 adjusted accordingly. The physician can, if desired, override the closed loop system. A microprocessor 74 can be included and incorporated into the closed loop system switch power on and off, as well as modulate the power. A suitable microprocessor is commercially available and well known to those skilled in the art of closed loop feedback systems. The closed loop system utilizes microprocessor 74 to serve as a controller, watch the temperature, adjust the RF power, look at the result, refed the result, and then modulates the power.

Figure 18:
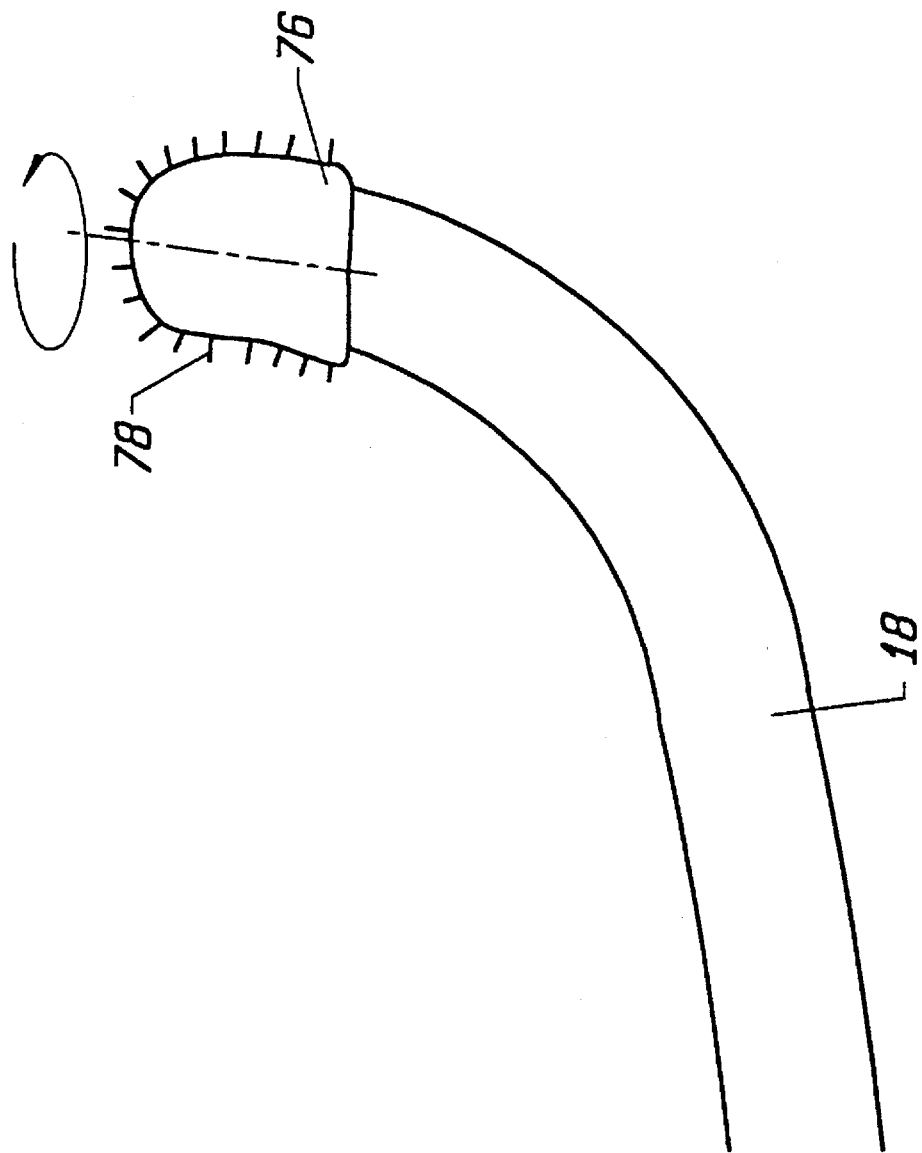
FIG. 18 is a perspective plan view of a roller element mounted at an electrode distal end according to the invention.

Optionally positioned on electrode distal end 18 is a conductive roller element 76 (FIG. 18). Conductive roller element is rotatably mounted on electrode distal end 18 and can include a plurality of projections 78. Roller element 76 is moved across the tissue site, along with projections 78, to deliver the thermal energy.

The present invention provides a method of contracting collagen soft tissue. The collagen soft tissue is contracted to a desired shrinkage level without dissociation and breakdown of the collagen structure. It can be used in the shoulder, spine, cosmetic applications, and the like. It will be appreciated to those skilled in the art that the present invention has a variety of different applications, not merely those specifically mentioned in this specification. Some specific applications include joint capsules, specifically the gleno-humoral joint capsule of the shoulder, herniated discs, the meniscus of the knee, in the bowel, for hiatal hernias, abdominal hernias, bladder suspensions, tissue welding, DRS, and the like.

RF energy, thermal energy, is delivered to collagen soft tissue. The thermal energy penetrates more than 1 mm through the collagen soft tissue. The penetration can be as much as about 3 mm. Electrode 14 is painted across the collagen soft tissue sequentially until the maximum shrinkage occurs. In one embodiment, the collagen soft tissue is contracted in an amount of about two-thirds of its resting weight. A temperature range of about 43 to 90 degrees C. is preferred. More preferred, the temperature range is about 43 to 75 degrees C. Still more preferred is a temperature range of 45 to 60 degrees C.

Figure 19:
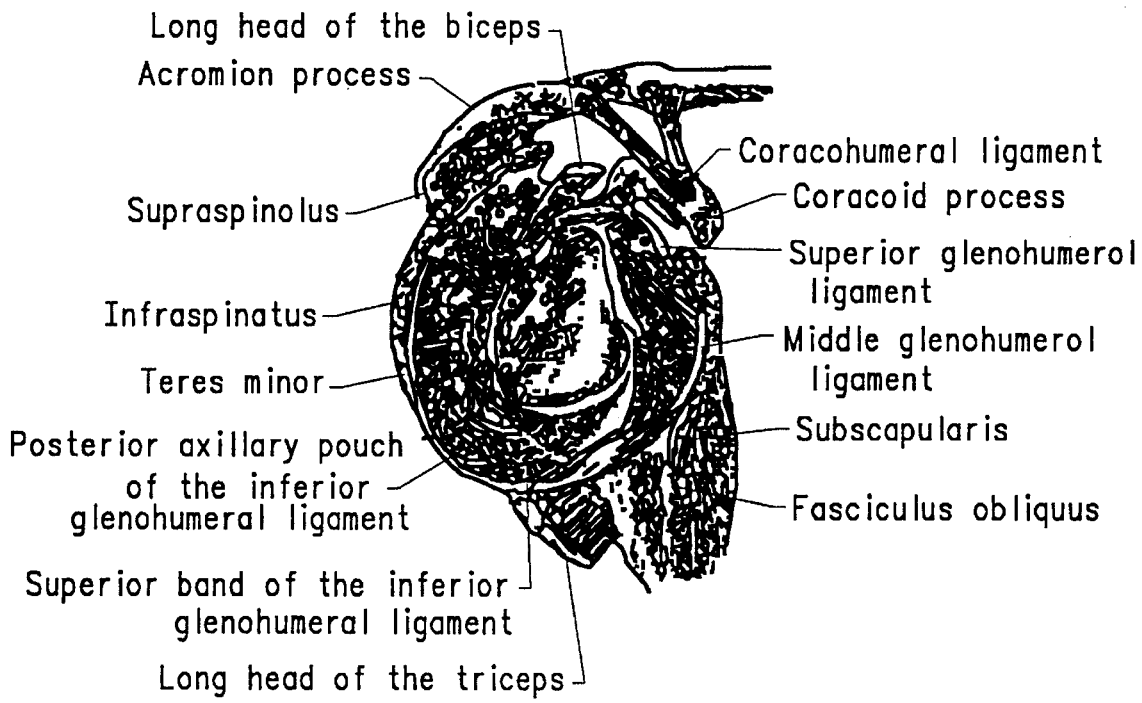
FIG. 19 is a drawing of the right glenohueral capsuloligamentous complex.

In one specific embodiment of the invention, joint capsules are treated to eliminate capsular redundancy. More specifically, the invention is utilized to contract soft collagen tissue in the gleno-humoral joint capsule of the shoulder. The basic anatomy of the gleno-humoral joint capsule of the shoulder is illustrated in FIG. 19.

The apparatus of the present invention provides RF heating in a fluid or saline environment to control thermal spread. RF heating is applied to collagen connective tissue shrinkage in temperature ranges of about 43 to 90 degrees C., 43 to 75 degrees C. and 45 to 60 degrees C. The RF energy is delivered through endoscopically guided handpiece 12 in a fluid or saline environment within the joint. It can be under arthroscopic visualization by the surgeon, or the apparatus can include a viewing device. The invention accurately controls the application of heat within a specific thermal range, and delivers thermal energy to collagen soft tissue of the joint, thereby contracting and restricting the soft tissue elasticity and improving joint stability. When applied to the shoulder, there is capsular shrinkage of the gleno-humoral joint capsule of the shoulder and a consequent contracture of the volume, the interior circumference, of the shoulder capsule to correct for recurrent instability symptoms. The degree of capsular shrinkage is determined by the operating surgeon, based on severity of preoperative symptoms and condition of the capsule at the time of arthroscopic inspection. The maximum amount of collagen contraction achieved is approximately two-thirds of its original structure.

Figures 20, 21:
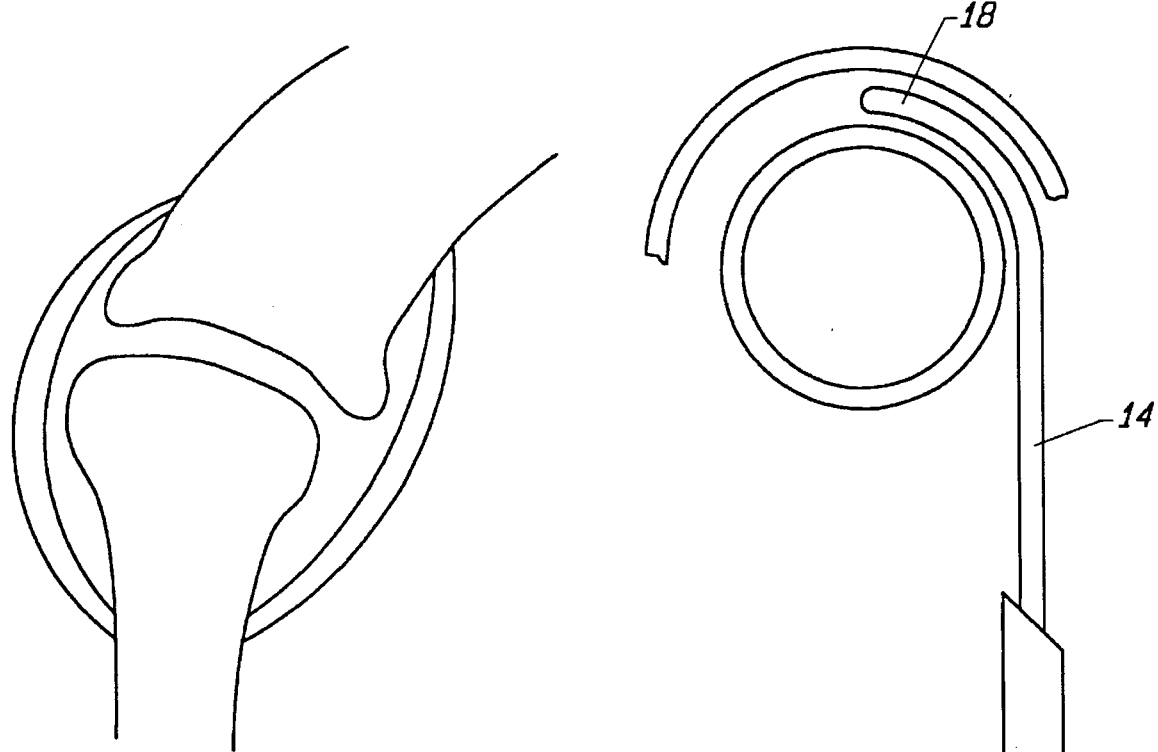
FIG. 20 is a drawing of a loose joint capsule.
FIG. 21 is a schematic drawing of the apparatus of the invention with an electrode supplying thermal energy to a joint structure.

In FIG. 20, a loose capsule is illustrated. The apparatus for control contraction of tissue of the present invention is applied to a joint capsule (FIG. 21). Electrode distal end 18 is painted across the surface of the collagen soft tissue.

FIGS. 23 and 24 illustrate the application of the invention to a herniated disc.

While embodiments and applications of this invention have been shown and described, it will be apparent to those skilled in the art that many more modifications than mentioned above are possible without departing from the invention concepts herein. The invention, therefore, is not to be restricted except in the spirit of the appended claims.

What is claimed is:

1. A method for repairing ligaments, joint capsules and connective tissue through the controlled contraction of collagen fibers, the method comprising:

providing an apparatus including a handle and an electrode having an electrode proximal end attached to the handle and an electrode distal end, the distal end including an energy delivering distal electrode portion having a surface with radiused edges for delivering substantially uniform energy across the surface of the energy delivering distal electrode portion;

positioning the energy delivering distal electrode portion adjacent to an area of collagen fibers to be contracted;

delivering substantially uniform energy across the surface of the energy delivering distal electrode portion to the area of collagen fibers; and contracting the collagen fibers through the application of energy to the collagen fibers.

2. The method of claim 1 further including the step of delivering an electrolytic solution to the area of collagen fibers, the electrolytic solution serving to provide a substantially uniform distribution of energy from the electrode to the collagen fibers.

3. The method of claim 1 further including the step of delivering an electrolytic gel to the area of collagen fibers, the electrolytic solution serving to provide a substantially uniform distribution of energy from the electrode to the collagen fibers.

4. The method of claim 1 further including the step of controlling the temperature of the collagen fibers to minimize the dissociation and breakdown of the collagen fibers and to minimize the ablation of tissue neighboring the collagen fibers.

5. The method of claim 1 further comprising the step of moving the energy delivering distal electrode portion relative to the area of collagen fibers being contracted during the delivery of energy to the area of collagen fibers in order to control the temperature of the collagen fibers so that dissociation and breakdown of collagen fibers is minimized and ablation of tissue neighboring the collagen fibers is minimized.

6. The method of claim 1, wherein the step of contracting the collagen fibers causes the collagen fibers to be contracted to about two-thirds of its initial size.

7. The method of claim 1, where the energy penetrates the collagen fibers to a depth of at least about 1 mm.

8. The method of claim 7, where the energy penetrates the collagen fibers to a depth of between about 1 and 3 mm.

9. The method of claim 9 further including the step of delivering an electrolytic solution to the area of collagen fibers, the electrolytic solution serving to provide a substantially uniform distribution of energy from the electrode to the collagen fibers, the electrolytic solution also serving to control the temperature of the collagen fibers.

10. The method of claim 9 further including the step of delivering an electrolytic gel to the area of collagen fibers, the electrolytic solution serving to provide a substantially uniform distribution of energy from the electrode to the collagen fibers, the electrolytic gel also serving to control the temperature of the collagen fibers.

11. The method of claim 1, wherein the energy delivering distal electrode portion delivers RF energy to the area of collagen fibers.

12. The method of claim 11, wherein the RF energy penetrates the collagen fibers to thermally contract the collagen fibers substantially without ablating neighboring tissue.

13. The method of claim 1, wherein the energy is applied only to the surface of the tissue.

14. The method of claim 1, wherein the step of positioning the energy delivering distal electrode portion includes positioning the energy delivering distal electrode portion adjacent to an area of collagen fibers in a joint capsule.

15. The method of claim 14 wherein the joint capsule is a gleno-humoral joint capsule of a shoulder.

* * * * *